United States Patent [19]

Spokane

[11] Patent Number: 5,298,144
[45] Date of Patent: Mar. 29, 1994

[54] CHEMICALLY WIRED FRUCTOSE DEHYDROGENASE ELECTRODES

[75] Inventor: Robert B. Spokane, Bellbrook, Ohio

[73] Assignee: The Yellow Springs Instrument Company, Inc., Yellow Springs, Ohio

[21] Appl. No.: 944,963

[22] Filed: Sep. 15, 1992

[51] Int. Cl.$^5$ ............................................ G01N 27/327
[52] U.S. Cl. .............................. 204/403; 204/153.12; 435/26; 435/817; 436/806
[58] Field of Search ............................ 204/153.12, 403; 435/817.26; 436/806

[56] References Cited

U.S. PATENT DOCUMENTS

| | | | |
|---|---|---|---|
| 4,840,893 | 6/1989 | Hill et al. | 435/6 |
| 5,089,112 | 2/1992 | Skotheim et al. | 204/403 |
| 5,177,012 | 1/1993 | Kim et al. | 204/403 |

FOREIGN PATENT DOCUMENTS 0278647 of 0000 European Pat. Off. .

OTHER PUBLICATIONS cis-BIS(2,2'-Bipyridine-N,N') Complexes of Ruthenium(III) (II) and Osmium (III)(II), Lay, P. A., Sargeson, A. M.; Taube, H., Inorg. Syn, 1986, 24, 291-306.
"Development of an On-line Glucose Sensor for Fermentation Monitoring," Brooks, S. L. et al., Biosensors 3 (1987/88) 45-56.
"D-Fructose Dehydrogenase of Gluconobacter Industrius: Purification, Characterization, & Appln. to Enzymatic Microdetermination of D-Fructose," Ameyama, M. et al., J. of Bacteriology, Feb. 1981, pp. 814-823.
"Electrical Wiring of Redox Enzymes," Heller, A., Accts. of Chemical Research, 1990, 23 pp. 128-134.
"Redox Polymer Films Containing Enzymes," Gregg, B. A. et al., J. Phys. Chem. 1991, 95, pp. 5976-5980.
"Redox Polymer Films Containing Enzymes," Gregg, B. A. et al., J. Phys. Chem. 1991, 95, pp. 5970-5975.

*Primary Examiner*—T. Tung
*Attorney, Agent, or Firm*—Biebel & French

[57] ABSTRACT

An enzyme electrode is disclosed for use in voltammetric systems wherein a PQQ dehydrogenase enzyme is chemically bonded to a water soluble polyvinylpyridine osmium bipyridine polymer. The enzyme and polymer are adsorbed onto the surface of the electrode with the polymer providing direct electron transfer from enzyme to electrode and vice-versa without the aid of additional mediators or electron shuttles added to the system.

8 Claims, 2 Drawing Sheets

1

CHEMICALLY WIRED FRUCTOSE DEHYDROGENASE ELECTRODES

FIELD OF THE INVENTION

The present invention pertains to enzyme electrodes of the type wherein a PQQ containing dehydrogenase enzyme is chemically bonded to an electroconductive polymer so as to facilitate electron transfer from a desired analyte to the electrode on which the polymer and enzyme are adsorbed.

BACKGROUND OF THE INVENTION

As set forth in "Electrical Wiring of Redox Enzymes," Heller, *Acc. Chem. Res.* Vol. 23, No. 5, 1990, in many enzymes, the redox centers thereof are located too remote from the outermost protein surface to be electrically accessible for purposes of providing direct electrical interaction between the enzyme and its associated electrode. Accordingly, it was difficult to promote chemical reactions by directly interacting the electrode and enzyme and it was similarly difficult to monitor chemical reactions involving the enzyme directly at the electrode. Due to the inaccessible nature of the redox centers of these enzymes, so-called mediators or electron shuttles have been physically admixed with the enzyme in a membrane or in the test system, or, in certain cases, the mediators or shuttles were chemically bonded to the enzyme to enhance electron transfer from a reactant or desired analyte through the enzyme to the electrode.

For example, mediated glucose sensors involving water soluble electron acceptors, such as ferricyanide, quinones, and various organic dyes have been tried. In European Patent Publication 0 278 647, modification of flavo protein enzymes such as glucose oxidase and D-amino acid oxidase through chemical attachment of electronically active materials thereto such as a ferroceneamide or a ferroceneacetamide is disclosed. Additionally, as reported in this publication, conversion of functional moieties on the enzymes, such as conversion of enzyme tyrosine-amides to enzyme dihydroxyphenylalanine amides, provides improvement in direct electrical interaction between enzyme and electrode.

In U.S. Pat. No. 4,840,893 (Hill et al.), a host of mediator enzyme systems is disclosed. Disclosed mediators include ruthenium complexes, ferrocenes, carbon-boron compounds, phenazine dyes, and metalloporphyrins. Enzyme/substrate pairs, whose behavior in association with mediator compounds has been purportedly studied, include flavo-proteins, PQQ enzymes, cytochrome b-linked enzymes, and metallo flavo proteins.

U.S. Pat. No. 5,089,112 teaches artificial redox compounds (i.e., mediators) that are covalently bound to a flexible polymer backbone. Disclosed polymers include siloxanes, polyphosphazene, poly(ethylene oxide) and poly(propylene oxide).

Redox-conducting epoxy cements, including conductive polyvinylpyridine osmium bipyridine polymers for use in chemically bonding with flavo protein enzymes, specifically glucose oxidase, are disclosed by Heller in the aforenoted Accounts of Chemical Research article and in "Redox Polymer Films Containing Enzymes. 1 A Redox-Conducting Epoxy Cement: Synthesis, Characterization, and Electrocatalytic Oxidation of Hydroquinone," *J. Phys. Chem.* 1991, 95, pp. 5970–5975.

Despite the efforts in the art, there remains a need to provide a conductive polymer that will chemically link (i.e., bond) to a PQQ based dehydrogenase enzyme to serve as an electron mediator or shuttle system so that direct electron transfer can be made from a reactant or analyte in contact with the enzyme to an electrode surface in contact with the enzyme-polymer mass.

More specifically, in the food and beverage industry, there is a need to provide for accurate determination of D-fructose concentration in liquids wherein an enzyme electrode containing PQQ based membrane bound fructose dehydrogenase enzyme is used in an amperometric measurement systems. Of further importance is the provision of a PQQ based membrane bound fructose dehydrogenase enzyme that is chemically bound to a water soluble, conductive polymer is contact with an electrode to provide for direct amperometric measurement without the requirement of additional mediator or electron shuttle moieties added to the reaction system.

BRIEF DESCRIPTION OF THE DRAWINGS

The invention will be further described with reference to the accompanying drawings, in which.

DETAILED DESCRIPTION OF THE PREFERRED EMBODIMENT

The present invention is directed to enzyme electrodes of the type commonly employed in electrochemical enzyme biosensors for use in liquid mixtures of various components for detecting the presence of or the concentration of a desired analyte. As described and shown herein, the electrode is specifically constructed of vitreous carbon, but it could also conveniently be prepared from gold, platinum or other chemically inert conductive materials. It can be used in a conventional two or three electrode voltammetric system with the auxiliary electrode present in the system preferably being composed of a platinum wire, and with a reference electrode composed of $Hg/Hg_2Cl_2$ or $Ag/AgCl$. In these systems, a predetermined polarized voltage is applied to the auxiliary electrode. The test electrode measures the current from the auxiliary electrode to the test electrode in microamps. As the analyte (here, fructose) concentration is increased in the solution, the current from the auxiliary electrode to the test electrode increases. The concentration of analyte in the solution can be determined due to the increase in current to the test electrode. The reference electrode has a very stable, reproducible potential which is used as a reference during calibration and measuring of the current from the auxiliary electrode to the test electrode.

The enzyme electrode is especially suited for measurement of fructose concentration in phosphate buffer solution via use of fructose dehydrogenase enzyme (EC 1.1.99.11) although it could be adapted to measure, for instance, any of the following analytes in combination with their corresponding PQQ based dehydrogenase enzyme.

| Analyte | PQQ Dehydrogenase Enzyme |
|---|---|
| glucose | glucose dehydrogenase |
| methanol and other alcohols | methanol dehydrogenase |
| methylamine | methylamine dehydrogenase |

Figure 1:
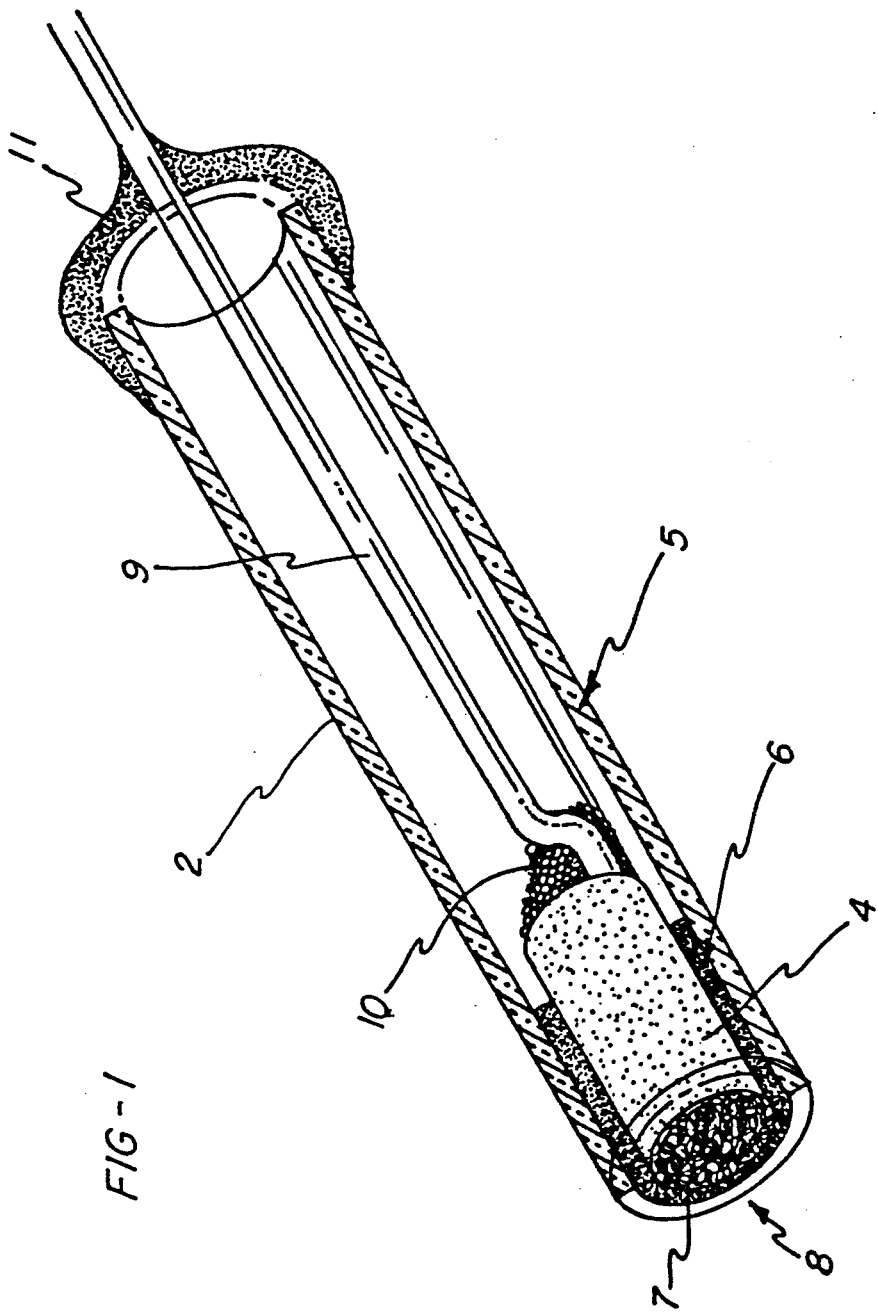
FIG. 1 is a perspective view of an enzyme electrode according to the present invention.

Turning now specifically to FIG. 1, there is shown an enzyme electrode 2 comprising a vitreous carbon rod 4 held in a central position inside a glass tube 5 by an epoxy seal 6. The carbon rod 4 has a coating 7 adsorbed thereon, at measuring surface 8 of the electrode. This coating comprises a conductive polymer and fructose dehydrogenase enzyme chemically bonded thereto. The coating 7 also comprises a crosslinking agent, such as a polyethyleneglycol diglycidyl ether which provides for crosslinking of the enzyme to the polymer. This coating provides for direct transfer of electrons from an analyte in contact therewith to the vitreous carbon surface on which the coating is adsorbed. Therefore, there is no need to add mediators to the solution.

The carbon rod 4 is coupled to an electrical contact wire 9 with an electrical conductive epoxy 10, such as a silver epoxy. The wire 9 and the top of the glass tube 5 are sealed with epoxy 11.

As to the conductive polymers that are employed, these are not new. They are the polyvinylpyridine/Os (bpy)$_2$Cl polymers reported supra. by Heller et al. that have been used to chemically wire to (i.e., bond with) flavoprotein enzymes such as glucose oxidase. It is unexpected, due to the difference in nature of respective active redox centers present, that a PQQ dehydrogenase type enzyme could be chemically wired with a polymer known to be successful in "wiring" flavoprotein enzymes. The flavoproteins contain flavin adenine dinucleotide (FAD) as their active redox centers whereas the PQQ enzymes contain pyrrolo quinoline quinone as the redox centers. These are quite different chemical moieties. They are structurally very different and carry out different redox processes. In some cases, the FAD based enzymes reduce oxygen to generate hydrogen peroxide. However, the PQQ based enzymes do not use oxygen as an electron carrier. They require another electron carrier to transfer the electron to the electrode. There is no reason to expect a PQQ enzyme to behave like an FAD one.

The hydrophilic water soluble polyvinylpyridine/Os (bpy)$_2$Cl polymers are made in accordance with the procedures set forth in Gregg and Heller, *J. Phys. Chem.* 1991, 95, pp. 5970-5975. Basically, as reported in this publication, (0.494 g, 0.864 mmol) of cis-bis(2,2'-bipyridine-N,N')dichloroosmium (II) and (0.430 g, 4.09 m equiv.) poly(4-vinylpyridine) mw≈50,000 are heated under a nitrogen blanket at reflux for 2 hours. The solution is then cooled to room temperature with 30 ml of DMF and 1.5 g of 2-bromoethylamine hydrobromide (7.3 mmol) being added. The solution is stirred at 45° C. overnight. The crude polymer is then precipitated via addition into acetone, with the hygroscopic precipitate collected, dissolved in H$_2$O, filtered and precipitated as a PF$_6$-salt by addition of NH$_4$PF$_6$ solution. This salt is then dissolved in acetonitrile, diluted with water and passed over anion exchange beads (Bio-Rad AG1-X4, chloride form) for 2 hours. The resulting solution is filtered and evaporated under vacuum conditions, Concentrated HCl is added to obtain pH of 2 and the solution is dripped into acetonitrile. The resulting precipitate is filtered and dried in a vacuum desiccator.

The reported estimated molar mass of the polymer repeat unit, as precipitated at pH2 is 1510 g/equiv. and the approximate structure of the polymer, as reported in the article, is

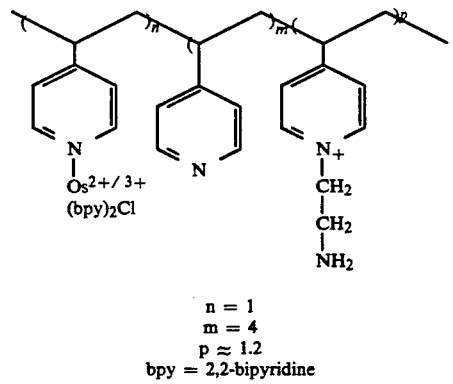

n = 1
m = 4
p ≈ 1.2
bpy = 2,2-bipyridine

Molecular weight of the entire macromolecule is probably around 50,000 or greater. The molecular weight is not critical. The only important criterion is the requirement that the polymer should be water soluble. Operable monomer molar ratio ranges are thought to be n=1, m=1-10, and p=1-10.

As to preparation of the precursor cis-bis(2,2'-bipyridine-N,N')dichloroosmium (II), this is reported at Lay, P. A., Sargeson, A. M.; Tauble, H., *Inorg. Syn,* 1986, 24, 291-306. As set forth in that article, bis(2,2'-bipyridine-N,N')dichloroosmium III chloride dihydrate is dissolved in a mixture of DMF and MeOH. A dilute aqueous solution of sodium dithionite is added to the mixture. The resulting solution is a dark purple oily suspension and is cooled in an ice bath. The complex crystallizes by scratching the beaker with a glass rod. The product is isolated via filtration and washed with water, MeOH, and diethylether. [The Bis(2,2'-byridine-N,N')dichloroosmium III chloride dihydrate is first prepared via Potassium hexachloroosmate (IV) reaction with 2,2'-bypyridine in DMF solvent under reflux. KCl crystals are removed via filtration with EtOH added to the filtrate. The complex is precipitated via slow addition of diethyl ether].

The fructose dehydrogenase which is used as the preferred PQQ based dehydrogenase enzyme is commercially available from Sigma under the F-4894 designation. It is solubilized and purified from the membrane fraction of glycerol-grown *Gluconobacter industrius* IFO 3260 by the techniques reported by Ameyama, et al., *J. Bacteriol.,* 145, 814 (1981). The purified D-fructose dehydrogenase is reported as an enzyme complex composed of dehydrogenase, cytochrome C and a third, unknown, peptide.

A crosslinking agent, preferably a diglycidylether molecule, such as a poly(ethyleneglycol) diglycidyl ether is used to effect crosslinking of the polymer to the enzyme via the ring opening of the epoxide moieties to form secondary amine linkages between enzyme amino and polymer amino groups (i.e. repeat unit p in the above structural formula).

As to the amounts of enzyme, polymer, and crosslinking agent that can be used to form the chemically wired PQQ dehydrogenase enzyme, these can vary over a wide range. However, based upon preliminary observations, as little as 1 mole of enzyme can be used for every 20 vinylpyridine repeat units present in the polymer to a high enzyme range content of 1 mole enzyme per 2 vinylpyridine repeat units.

The preferred poly(ethyleneglycol) diglycidyl ether may be used in an amount of from about 0.001–1.0 mg per mg of polymer used.

To make the enzyme electrode, an aqueous solution containing the polymer and a phosphate buffer solution of enzyme are applied to the carbon electrode surface. The poly(ethyleneglycol) diglycidylether cross linker is also supplied in phosphate buffer solution form over the desired electrode surface. The components are mixed on the surface, for example, by a syringe tip or the like and are allowed to dry for about 2 hours at 25° C. The electrodes are stored dry in the dark at about 4° C. between uses.

The invention will be further described in conjunction with the following examples, which should be viewed as being illustrative of the invention and not to limit the scope thereof.

EXAMPLE

Chemical wiring of fructose dehydrogenase to a vitreous carbon electrode by the osmium bipyridine polymer is described.

There are three critical components of the wired electrodes. These include the fructose dehydrogenase (Sigma F-4892), the osmium bipyridine polymer made in accordance with the procedures, detailed supra., and a 3 mm diameter vitreous carbon electrode (V-10 Atomergic).

The fructose dehydrogenase is a three-part enzyme complex which is membrane bound (Ameyama, et al., *J. Bacteriol.*, 145, 814 (1981). The enzyme does not require NAD for functionality. The complex includes a dehydrogenase component, a cytochrome C component and a third protein whose function has not yet been determined. The enzyme is stable in buffer with 0.1M citrate, 0.1M phosphate and 0.1% Triton X-100 at Ph 5.0. This buffer was used for all enzyme solutions, including electrode preparation, fructose analysis and fructose dehydrogenase storage.

The vitreous carbon electrode is polished with a series of alumina micropolishes (Buehler) with a 0.05 um alumina particle size used as the final polish. The electrodes are made by applying the following solutions in the order noted to a polished vitreous surface: first 0.5 microliters of 10 mg/ml polymer solution, then 0.5 microliters of 1000 units/ml enzyme solution and lastly 0.25 microliters of 2.9 mg/ml PEG-DGE 400 solution (Polyethylene glycol diglycidylether 400-Polysciences). The components are mixed with the tip of a syringe and allowed to dry for 2 hours at 25° C. The electrodes are stored dry in the dark at 4° C. between uses.

The electrodes were tested at room temperature in a stirred cuvette with 30 ml. of buffer. Fructose measurements were done by the sequential addition of 30 mM fructose solution to the cuvette. Electrode polarization was maintained with an Omni-90. The reference electrode used was a Bioanalytical Systems Ag/AgCl. The auxiliary electrode was a 28 gauge platinum wire. The polarizing voltage used was +0.4 volts.

Results and Discussion

Figure 2:
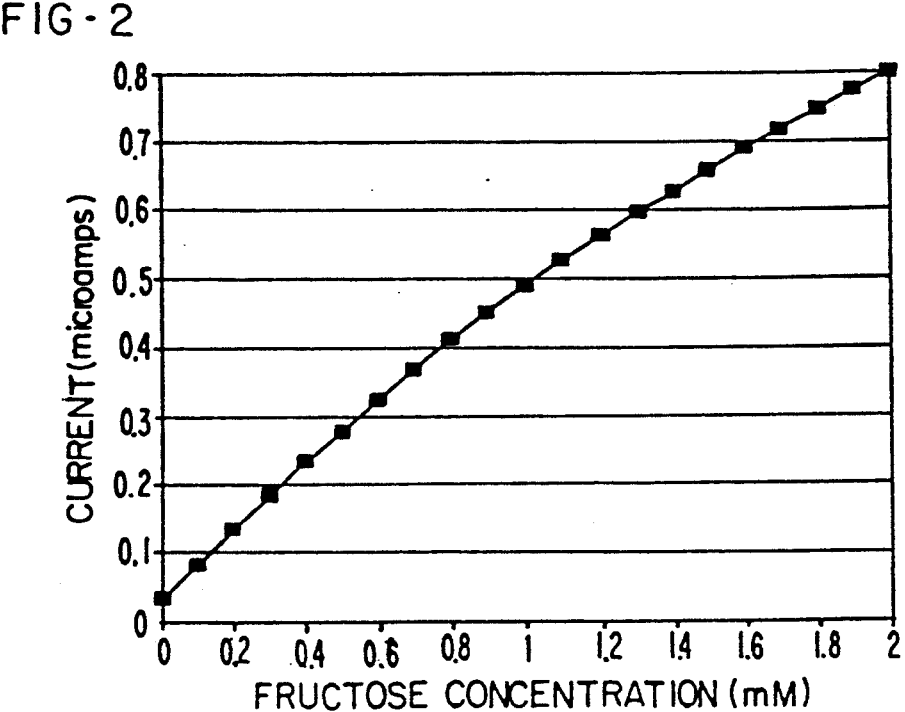
FIG. 2 is a calibration curve graph resulting from a series of amperometric measurements made for fructose concentration using enzyme electrodes in accordance with the invention.

There were four electrodes prepared for these experiments. They all had comparable initial activities. The calibration curve derived from a series of sequential injections can be seen in FIG. 2. The measurements were taken at the plateau after a 30 second equilibration period. The plateau was reached after approximately 15 seconds. The current density for the 1 mM fructose solution was 7.1 microamperes/square centimeter.

Figure 3:
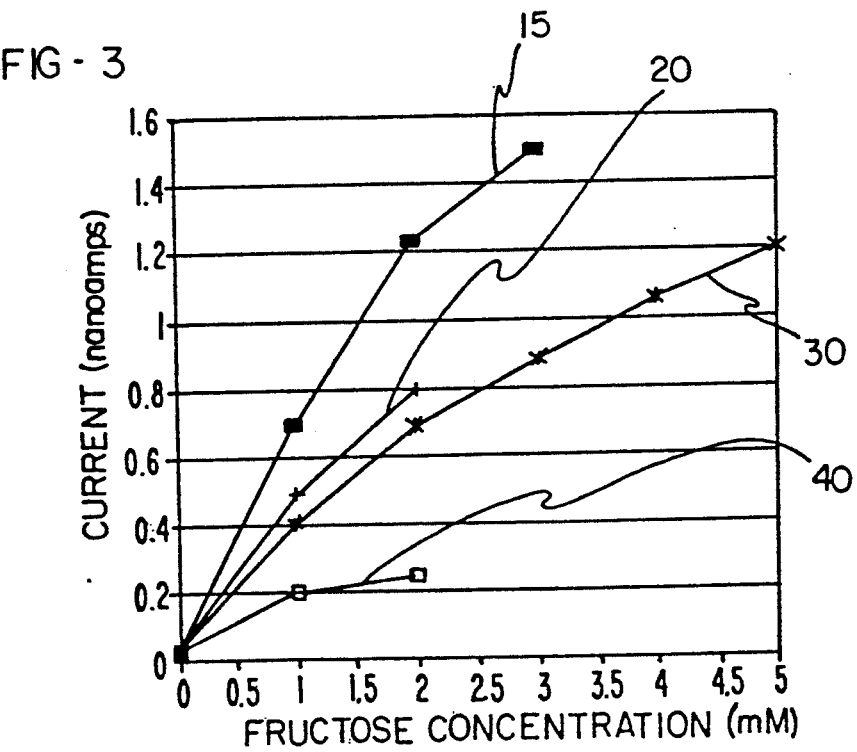
FIG. 3 is a graph showing individual amperometric measurements made for varying concentrations of fructose with a plurality of sequentially used enzyme electrodes in accordance with the invention.

Turning to FIG. 3, line 15 represents the calibration curve resulting from the first enzyme electrode test, lines 20 and 30, respectively, indicate test results taken 30 min. and 45 min., respectively, after the start of the first test. Line 40 is the calibration curve derived from tests performed one day after preparation of the electrodes. After each sequential test, a decrease in the activity of the electrode was observed. This can be seen in FIG. 2. The sensor utilized to derive curve 40 was stored dry at 4° C. between day 0 and day 1.

These results demonstrate that the amperometric response to fructose concentration is linear over the concentration range up to about 0.8 m/molar for this particular formulation and that the non-linearity increases as the activity of the enzyme decreases. The activity decreased over 5 fold by the second day of testing. These observations suggest that the number of available enzyme sites is decreasing over this period of time.

In additional testing, the activity of an unused electrode which was stored dry remained high relative to wet storage in the buffer.

These experiments demonstrate that the PQQ containing dehydrogenases can be chemically wired (bonded) to a vitreous carbon electrode surface using the prior art osmium bipyridine polymers that were developed by Heller et al. to chemically wire glucose oxidase to a carbon electrode. Although applicant is not to be bound to any particular theory of operation, it is thought that the electron transfer capabilities of this fructose dehydrogenase enzyme complex are probably based upon the transfer of the electron to the cytochrome C within the complex. The cytochrome C then may transfer the election to the osmium polymer.

While I have shown and described herein certain embodiments of the present invention, it is intended that there be covered as well any change or modification therein which may be made without departing from the spirit and scope of the invention as defined in the appended claims.

What is claimed is:

1. An enzyme electrode for measuring D-fructose concentration in liquids comprising:
   (a) a fructose dehydrogenase enzyme containing pyrrolo quinoline quinone cofactor;
   (b) a conductive polymer comprising a water soluble polyvinylpyridine complex of Os(bipyridine)$_2$ Cl; and
   (c) an electron collector, said conductive polymer being chemically bonded to said enzyme and adsorbed on said electron collector, said enzyme electrode being devoid of electron mediator save for said conductive polymer.

2. An electrode as recited in claim 1 further comprising a crosslinking agent for crosslinking said polymer to said enzyme.

3. An electrode as recited in claim 2 wherein said enzyme is membrane bound fructose dehydrogenase from Gluconobactor Species.

4. An electrode as recited in claim 3 wherein said conductive polymer is a water soluble polymer having the structure

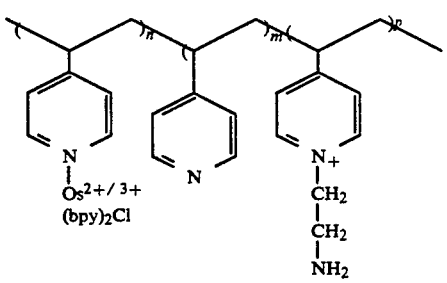
wherein
bpy=2,2'-bypyridine
wherein n=1
m=1-10
p=1-10.
5. Electrode as recited in claim 4 wherein m=4 and p≈1.2.
6. Electrode as recited in claim 3 wherein said cross-linking agent is an epoxide.
7. Electrode as recited in claim 6 wherein said epoxide is a poly(ethyleneglycol) deglycidylether.
8. Electrode as recited in claim 3 wherein said electron collector is a vitreous carbon surface.
* * * * *